United States Patent [19]
Bonnette et al.

[11] Patent Number: 5,989,271
[45] Date of Patent: Nov. 23, 1999

[54] FLEXIBLE TIP RHEOLYTIC THROMBECTOMY CATHETER AND METHOD OF CONSTRUCTING SAME

[75] Inventors: Michael J. Bonnette, Afton; John Edward Morris, Minneapolis; Steven E. Wiesel, Montrose; Cindy M. Setum, Plymouth; Robert C. Dutcher, Maple Grove; William J. Drasler, Minnetonka, all of Minn.

[73] Assignee: Possis Medical, Inc., Minneapolis, Minn.

[21] Appl. No.: 09/188,631

[22] Filed: Nov. 9, 1998

[51] Int. Cl.⁶ .................................................. A61B 17/22
[52] U.S. Cl. ........................... 606/159; 604/22; 606/167; 606/170
[58] Field of Search ........................... 604/19, 22; 606/1, 606/127, 159, 167, 170

[56] References Cited

U.S. PATENT DOCUMENTS 5,320,599  6/1994  Griep et al. .............................. 606/159
5,370,609  12/1994  Drasler et al. ........................... 606/159

Primary Examiner—Glenn K. Dawson
Attorney, Agent, or Firm—Hugh D. Jaeger

[57] ABSTRACT

A rheolytic thrombectomy catheter and method of using same to remove thrombus from a body vessel or other body cavity. The rheolytic thrombectomy catheter has a first tube with a distal open end and a second tube aligned within the first tube and having a flexible tip assembly. A tapered and flexible tip follows a guidewire within and along tortuous and difficult vasculature paths to the site of thrombus. The flexible tip assembly, includes a soft flexible tip and also includes a hard plastic shell offering structural integrity and rigid alignment between a toroidal loop and an inner body to prevent lever arm distortion and to maintain spray gap alignment for saline jet flow emanating from the toroidal loop. Saline jets dislodge, entrain, and break thrombus into pieces which are evacuated through the dual lumen tube. A construction method is also included for mounting of the toroidal loop within the hard plastic shell and attachment of the soft tapered and flexible tip with sufficient bond strength to function as intended for use.

19 Claims, 10 Drawing Sheets

FLEXIBLE TIP RHEOLYTIC THROMBECTOMY CATHETER AND METHOD OF CONSTRUCTING SAME

BACKGROUND OF THE INVENTION

1. Field of the Invention

The present invention relates to a flexible tip rheolytic thrombectomy catheter and method of using same for removal of thrombus from a body vessel or other body cavity and to a method of constructing the same.

2. Description of the Prior Art

Procedures and apparatus have been developed for ease in removing tissue and various deposits from the human body. Several such devices employ a jet of saline as the working tool to help break up the tissue deposit and further provide a suction means to remove the deposit. U.S. Pat. No. 5,135,482 to Neracher describes a hydrodynamic device for removal of organic deposit from a human vessel. A supply of saline is delivered by a high pressure duct to the distal end of a catheter. The saline exits the duct as a jet that is directed generally forward and directly toward the tissue to be broken up. The duct is contained within and can move axially with respect to a hose that is positioned around the duct. A vacuum suction is applied to the hose to remove the debris that is created from the broken-up tissue. This device is not intended to pass through tortuous pathways found in the fragile vessels of the heart, and any attempt to employ the device for such purpose would be far too traumatic to the patient.

Another drainage catheter, described by Griep in U.S. Pat. No. 5,320,599, has a discharge channel and a pressure channel. The channels are formed into a single catheter tube such that the two tubes are fixed with respect to each other. This catheter could not provide the flexibility needed to negotiate the tortuous vascular pathways found in the vessels of the heart.

SUMMARY OF THE INVENTION

The general purpose of the present invention is to provide a flexible tip rheolytic thrombectomy catheter for removal of thrombus from a body vessel or other body cavity and a method of constructing the same.

The present invention, a flexible tip rheolytic thrombectomy catheter, is a surgical device which is advanced through tortuous vasculature for subsequent removal of material such as thrombus from a vessel or other body cavity. As shown in one or more embodiments, a flexible tip rheolytic thrombectomy catheter for removing tissue from a vessel or other body cavity includes an outer assembly comprising a first or dual lumen tube with an open distal end and having a large and a small lumen; and an inner assembly comprising a high pressure second or hypo-tube having a high pressure lumen. The outer assembly and the inner assembly are shown as separate units for purposes of illustration and together form flexible tip rheolytic thrombectomy catheter which is operated as a single unit catheter.

Preferably, the flexible tip rheolytic thrombectomy catheter has a tapered and flexible tip which is attached at the distal end of a flexible tip assembly to allow advancement of the inner assembly and the outer assembly together as a single unit catheter within vasculature of a tortuous nature, as well as along vasculature which is not necessarily tortuous. Preferably, the flexible tip rheolytic thrombectomy catheter includes a high pressure hypo-tube, residing in and extending beyond the small lumen of the dual lumen tube, the end of which is shaped in the form of a toroidal loop for directing one or more jets of saline to impinge upon thrombotic tissue at or near the distal end of the dual lumen tube. The large lumen of the dual lumen tube functions as an evacuation tube and as a passageway for a guidewire. The flexible tip rheolytic thrombectomy catheter preferably is flexible and can pass over a standard guidewire through tortuous vascular pathways.

The present invention also provides a method of removing thrombus from an obstructed body vessel. The method includes the steps of:

a. advancing a guidewire through a tortuous or non-tortuous path to a vascular site containing thrombus;

b. advancing the flexible tip rheolytic thrombectomy catheter over the guidewire to the vascular site containing thrombus to position the distal end at the vascular site;

c. providing a high pressure saline supply to the hypo-tube so as to cause a jet of saline to emanate in a proximal direction from the flexible tip assembly to entrain thrombus; and, d. providing a route and appropriately applied pressure for evacuation of thrombus at a manifold.

In the method, preferably, the flexible tip assembly carries a distally projecting tapered and flexible tip to facilitate further distal advancement of the catheter within the vasculature to a further vascular site containing thrombus so as to remove additional distally situated thrombus.

The present invention is a catheter combination made with a first or dual lumen tube, being a part of an outer assembly, the dual lumen tube having a proximal end, an open distal end, and a web member extending along the interior of the dual lumen tube which defines a large lumen and a small lumen each extending between the proximal end and the open distal end; a second or hypo-tube, being a part of an inner assembly, the hypo-tube being aligned in the small lumen of the dual lumen tube, the hypo-tube having a proximal end, a distal end, and a lumen extending between the proximal end and the distal end; and a flexible tip assembly, being also a part of the inner assembly, the flexible tip assembly being located at the hypo-tube distal end and including the termination of the hypo-tube which is formed into a toroidal loop having rearwardly facing jets for directing fluid exiting the lumen of the hypo-tube, a hard plastic shell having a rearwardly or proximally facing orifice and an annular curved portion juxtaposing and anchoring the toroidal loop, a tubular support extension extending rearwardly or proximally from the hard plastic shell to accommodate and support the end of the hypo-tube proximal to the toroidal loop, and a tapered and flexible tip proximally secured within the distal end of the hard plastic shell.

The flexible tip rheolytic thrombectomy catheter functions to improve the guidewire tracking of the catheter by incorporation of a flexible tip assembly including a soft tapered and flexible tip of polyether block amide, or other suitable material, which can also be radio-opaque, thereby allowing the catheter distal end to flex, to track, and to be led through vessel junctions or tortuous path vessels having angular displacement without binding or hanging up during tracking. The flexible tip assembly improves the tracking of the catheter along a guidewire by creating a stiffness transition zone between the extreme distal catheter tip (tapered and flexible tip) and the relatively stiff, gap region of the flexible tip assembly at the distal catheter end wherein the distal hypo-tube end is held in a fixed position (90°) to the toroidal loop which is fixed by adhesive in a shell of hard polycarbonate plastic or other suitable shell material. The stiffness transition zone acts to guide, direct and to lead the stiff gap region in the proper tortuous direction and to be taken and led through a turn rather than to be allowed to continue in a straight direction or to bind or hang up during a transition from one vessel to another vessel. Another consideration is that the flexible and tapered tip does not act as a lever arm, when negotiating vessel bends or transitioning from vessel to vessel, which can result in the subsequent distortion of the 90-degree alignment of the toroidal loop to the distal hypo-tube end, which would be detrimental to jet alignment. This distortion is alleviated by a proximally extending support extension of the hard polycarbonate plastic shell which, with the hard plastic shell and the toroidal loop secured within, serves to protect the 90-degree alignment from being subjected to lever forces, in addition to creating a certain amount of give in the flexible tip assembly to lessen forces acting adversely to gap alignment. Unique to the design is the strength of the bond between the distally located toroidal loop (which is metal) and the soft urethane tapered and flexible tip which is achieved by the use of the intermediate hard polycarbonate shell component. The high strength bond between the plastic of the hard shell and the metal of the toroidal loop is important to maintain the parallel and concentric relationship between the toroidal loop and an inner body at the aligned dual lumen tube distal end from lever forces created by the tip assembly.

One significant aspect and feature of the present invention is a toroidal loop which is oriented to direct jets of saline in a proximal direction.

Another significant aspect and feature of the present invention is a toroidal loop having jets located on and distributed along the locus of a circle whose center is concentric with the toroidal loop, and located on the proximal toroidal loop region.

Another significant aspect and feature of the present invention is a tip assembly comprising a hard plastic shell, a tubular support extension extending proximally from the hard plastic shell, a toroidal loop aligned within the hard plastic shell, and a soft tapered and flexible tip extending distally from the hard plastic shell.

Yet another significant aspect and feature of the present invention is a hard plastic shell having a proximally oriented open orifice surrounding a greater portion of and providing for fixation of a toroidal loop to the interior of the hard plastic shell.

Still another significant aspect and feature of the present invention is a hard plastic shell having a tubular support extension for accommodation of one end of a hypo-tube to maintain the parallel and concentric relationship between the toroidal loop and an inner body at the aligned dual lumen tube distal end from lever forces created by the flexible tip assembly.

A further significant aspect and feature of the present invention is a soft tapered and flexible tip provided at the distal end of the catheter to allow advancement of the catheter within the vasculature.

A still further significant aspect and feature of the present invention is a soft tapered and flexible tip which is distally more flexible and distally more limber for successful initial entry into a branch vessel followed by a progressive limberness decrease proximally for steering of the distal catheter end subsequent to initial branch vessel entry.

Having thus described embodiments and significant aspects and features of the present invention, it is the principal object of the present invention to provide a flexible tip rheolytic thrombectomy catheter for removal of thrombus from a body vessel and a method of constructing the same.

One object of the present invention is to provide a flexible tip rheolytic thrombectomy catheter of such size, flexibility and construction as to enable it to pass readily through the tortuous pathways found in the fragile vessels of the heart or other body vessels.

Another object of the present invention is to provide a flexible tip rheolytic thrombectomy catheter with means for producing one or more jets of saline and projecting them in a proximal direction toward a site of thrombus and toward an evacuation passage.

A further object of the present invention is to provide an improved method of removing thrombus from an obstructed body vessel.

A further object of the present invention is a flexible tip symmetric over-the-wire thrombectomy catheter with a flexible plastic tip bonded to a metal toroidal loop with sufficient bond strength to prevent catastrophic failure of the bond resulting in foreign body embolization.

A further object of the present invention is a catheter of small dimension to be allowed access to small tortuous path vessels.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
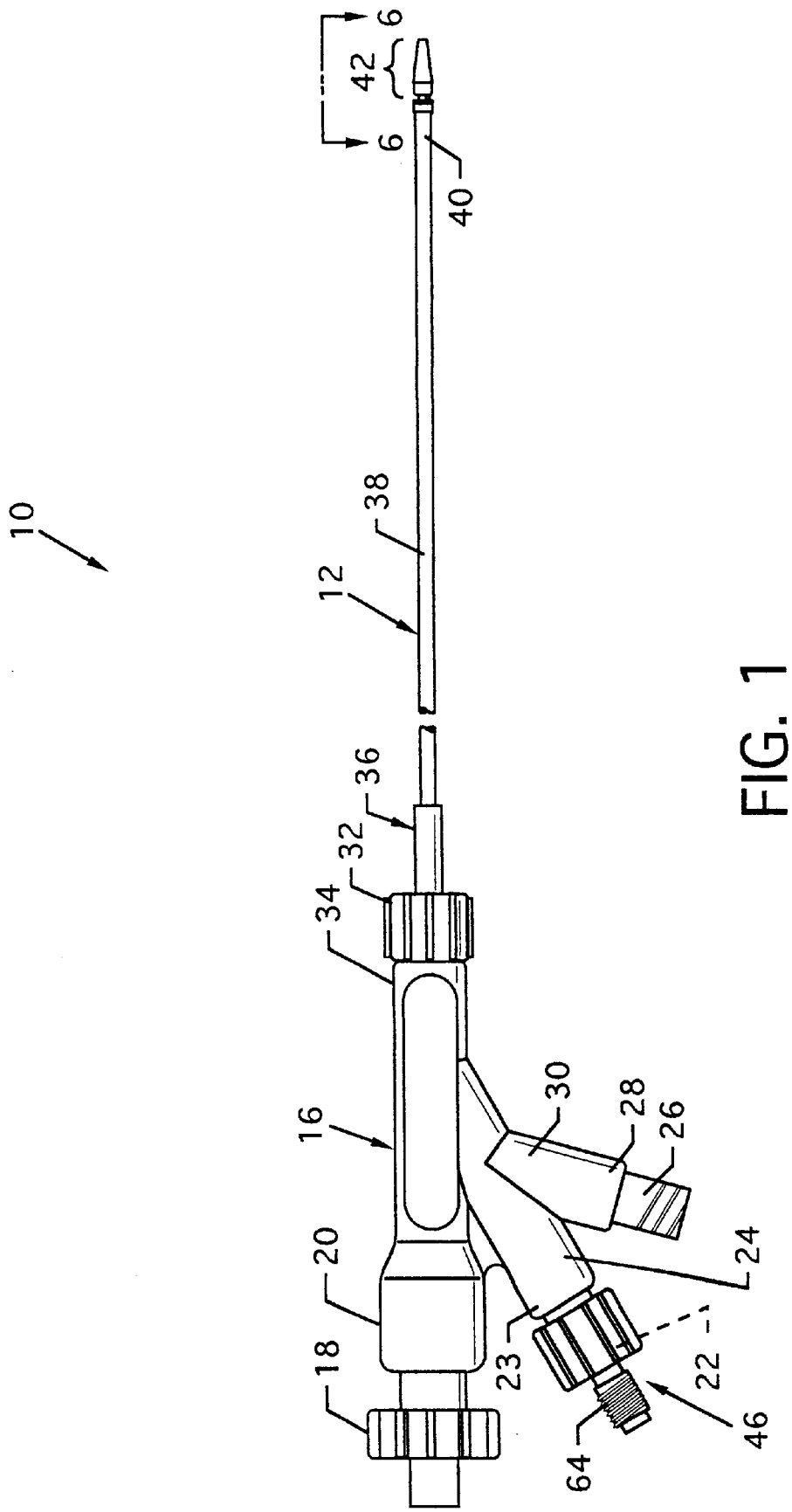
FIG. 1 is a side view of the present invention, a flexible tip rheolytic thrombectomy catheter useful for the removal of thrombus.
Figure 2:
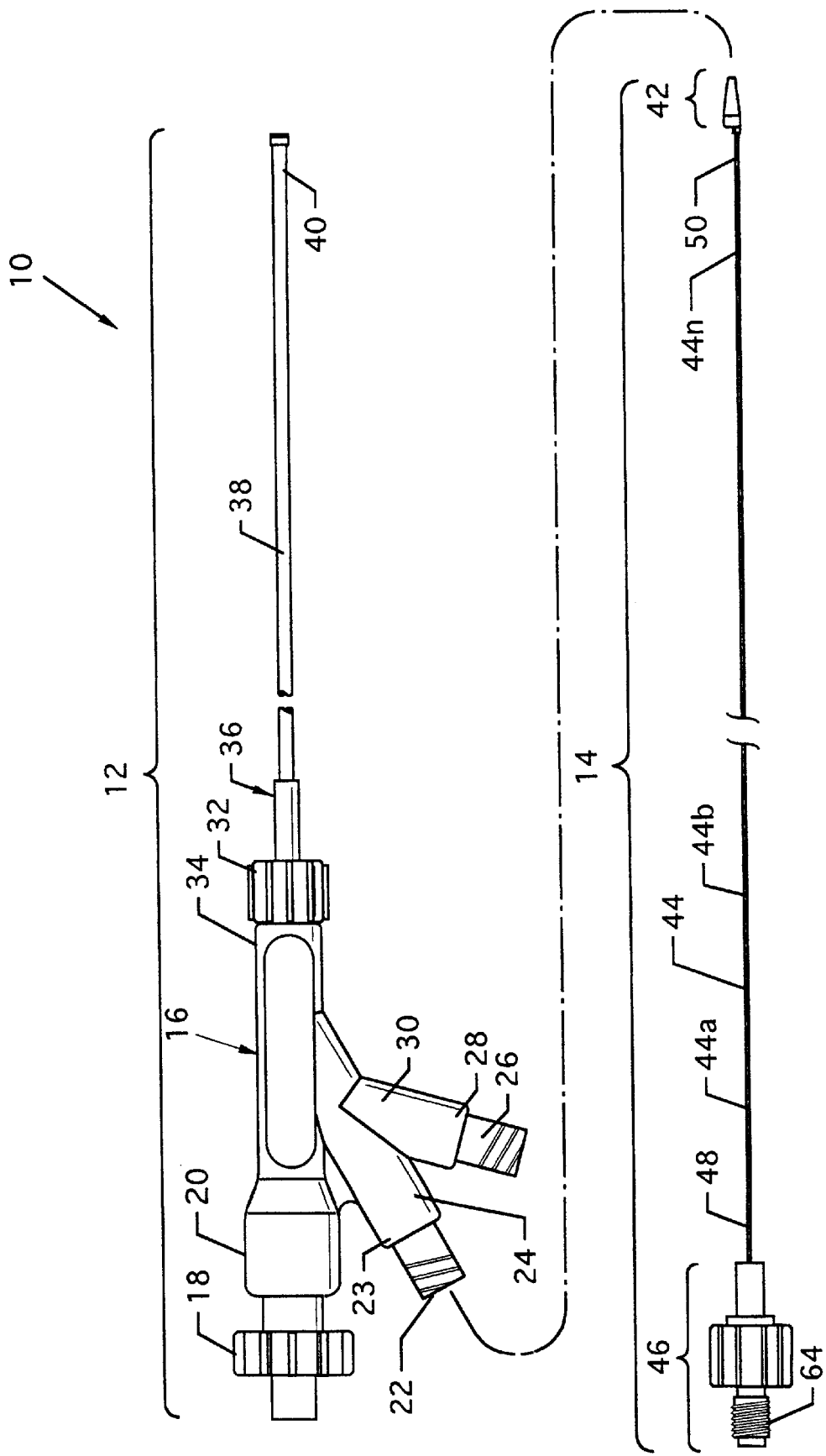
FIG. 2 is a semi-exploded side view of the flexible tip rheolytic thrombectomy catheter depicting the two major assemblies thereof, viz., an outer assembly and an inner assembly.

FIG. 1 illustrates a side view of a flexible tip rheolytic thrombectomy catheter 10 useful for the removal of thrombus, and FIG. 2 illustrates a semi-exploded side view of the flexible tip rheolytic thrombectomy catheter 10. The flexible tip rheolytic thrombectomy catheter 10 includes two major assemblies: namely, an outer assembly 12 and an inner assembly 14. The outer assembly 12 and the inner assembly 14 are illustrated as separated, for the purpose of clarity, but in actual practice the majority of inner assembly 14 resides within the outer assembly and remains stationary with respect to the outer assembly 12. The inner assembly 14 is constructed to fixedly align and to be held by a small lumen 47 of the dual lumen tube 38 (FIG. 6) and extends beyond the length of the outer assembly 12 where it is concentrically aligned within the outer assembly 12. Externally visible components, or portions of components, of the outer assembly 12 of the rheolytic thrombectomy catheter 10, as illustrated in FIGS. 1 and 2, include a manifold 16, a hemostasis nut 18 secured in the proximal end 20 of the manifold 16, a Luer connection 22 located at the proximal end 23 of an angled manifold branch 24 extending from the manifold 16, a Luer connection 26 located at the proximal end 28 of an angled manifold branch 30 extending from the manifold 16, Luer fitting 32 secured to the distal end 34 of the manifold 16, a strain relief 36 secured to the distal end 34 of the manifold 16 by the Luer fitting 32, a first or dual lumen tube 38 of polyether block amide, polymer or other suitable materials, having a distal end 40 secured to the manifold 16 by the strain relief 36 and Luer fitting 32, and a flexible tip assembly 42 located at and aligned to and attached to, the distal end 40 via a second or hypo-tube 44. The externally visible components of the inner assembly 14, illustrated in FIG. 2, include a high pressure second or hypo-tube 44, a filter housing/high pressure connection assembly 46 concentrically aligned to and secured over and about the hypo-tube proximal end 48, and the flexible tip assembly 42 at the hypo-tube distal end 50. The high pressure hypo-tube 44 is drawn and is tapered in incremental steps to provide degrees of flexibility along its length. For purposes of example and illustration, the hypo-tube 44 can include a hypo-tube portion 44a at the hypo-tube proximal end 48 having an outer diameter range of 0.015 to 0.025 inches, and can include a plurality of incrementally stepped down hypo-tube portions 44b–44n each of lesser outer diameter, where the last hypo-tube portion 44n is stepped down to an outer diameter range of 0.015 to 0.008 inches or less at the hypo-tube distal end 50. The hypo-tube 44 becomes increasingly more flexible from the hypo-tube proximal end 48 towards the hypo-tube distal end 50 due to the incremental diameter decrease along its length. Increasing flexibility along the length of the hypo-tube 44 allows for easier flexed penetration into tortuous vascular paths. Although the hypo-tube 44 is stepped down in increments, the hypo-tube 44 can also be fashioned of a constantly decreasing outer diameter to provide increasing flexibility along its length and shall not be construed to be limiting to the scope of the invention. The tapered and flexible tip is characterized by a length to maximum diameter ratio of 1 to 10.

Figure 3:
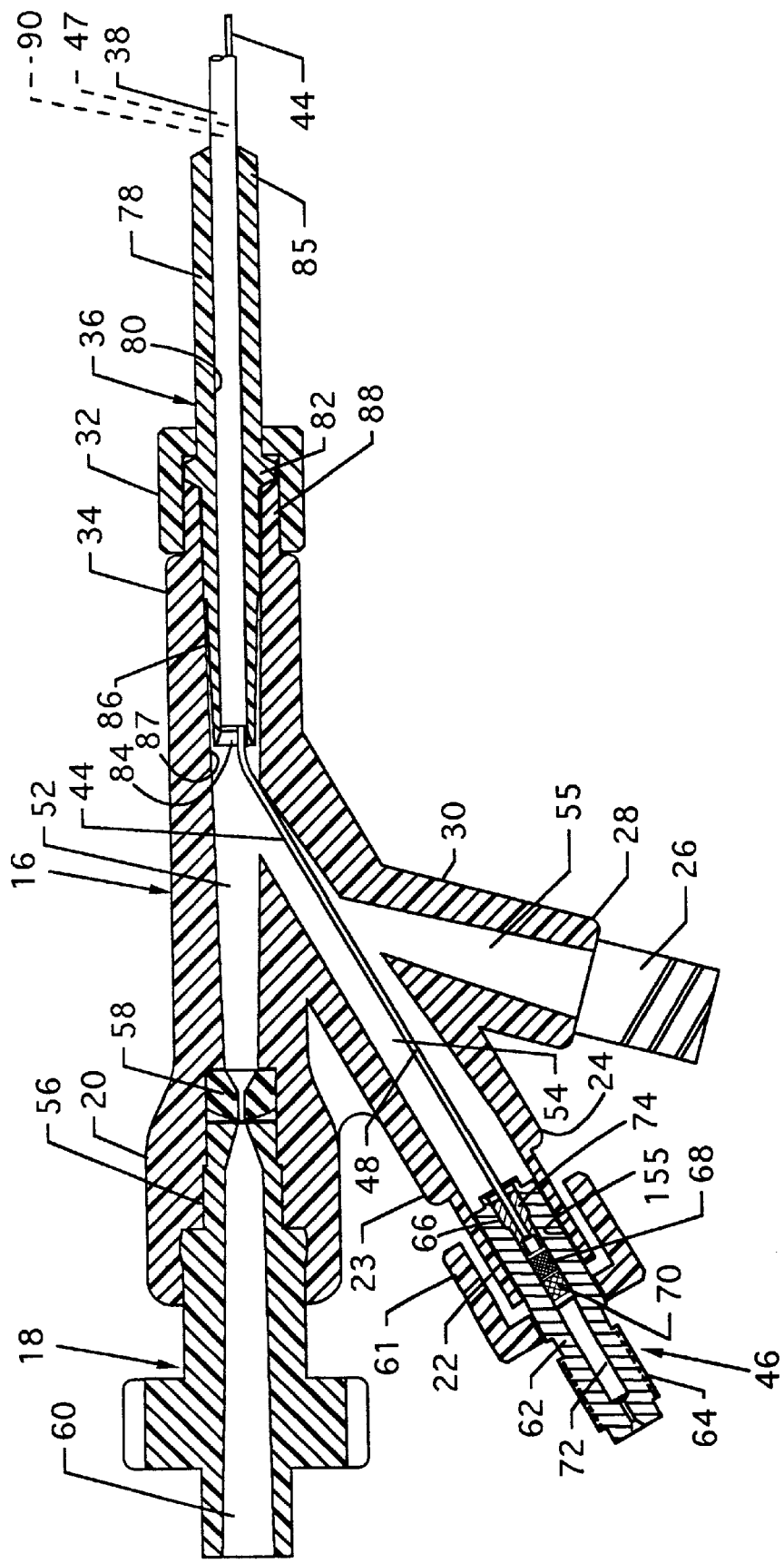
FIG. 3 is a cross sectional side view of a manifold and adjacent components constituting parts of the outer assembly.

FIG. 3 illustrates a cross sectional side view of the manifold 16 and adjacent components, where all numerals correspond to those elements previously or otherwise described. The manifold 16 includes a tapered centrally located main passage 52 aligned along the longitudinal axis of the manifold 16, a branch passage 54 extending along the axis of the branch 24 which intersects and is connected to the centrally located main passage 52, and another branch passage 55 extending along the axis of the branch 30 and intersecting the passage 54 of branch 24. The manifold proximal end 20 houses a multi-radius cavity 56 for accommodation of the hemostasis nut 18 and an O-ring 58 which is compressed by action of the hemostasis nut 18 to act as a seal with or without a guidewire in place. A passage 60 aligns centrally to the longitudinal axis of the hemostasis nut 18 and connects to the centrally located main passage 52, which is tapered so as to aid the front loading of a guidewire with the use of a guidewire introducer.

Luer connection 22 extends from the angled manifold branch 24 of the branch proximal end 23. The filter housing/high pressure connection assembly 46, which is secured to the Luer connection 22 by a Luer fitting 61, includes a cylindrical-like body 62 having a threaded external surface 64, a tubular cavity 66, fine and coarse filters 68 and 70 residing in the tubular cavity 66, a central passage 72 extending through the body 62 and connecting with the tubular cavity 66, and an anchoring plug 74 within the tubular cavity 66 into which the hypo-tube 44 proximal end 48 suitably secures. The central passage 72 communicates through the fine and course filters 68 and 70 with the centrally located lumen 76 (FIG. 4) of the hypo-tube 44.

Figure 6:
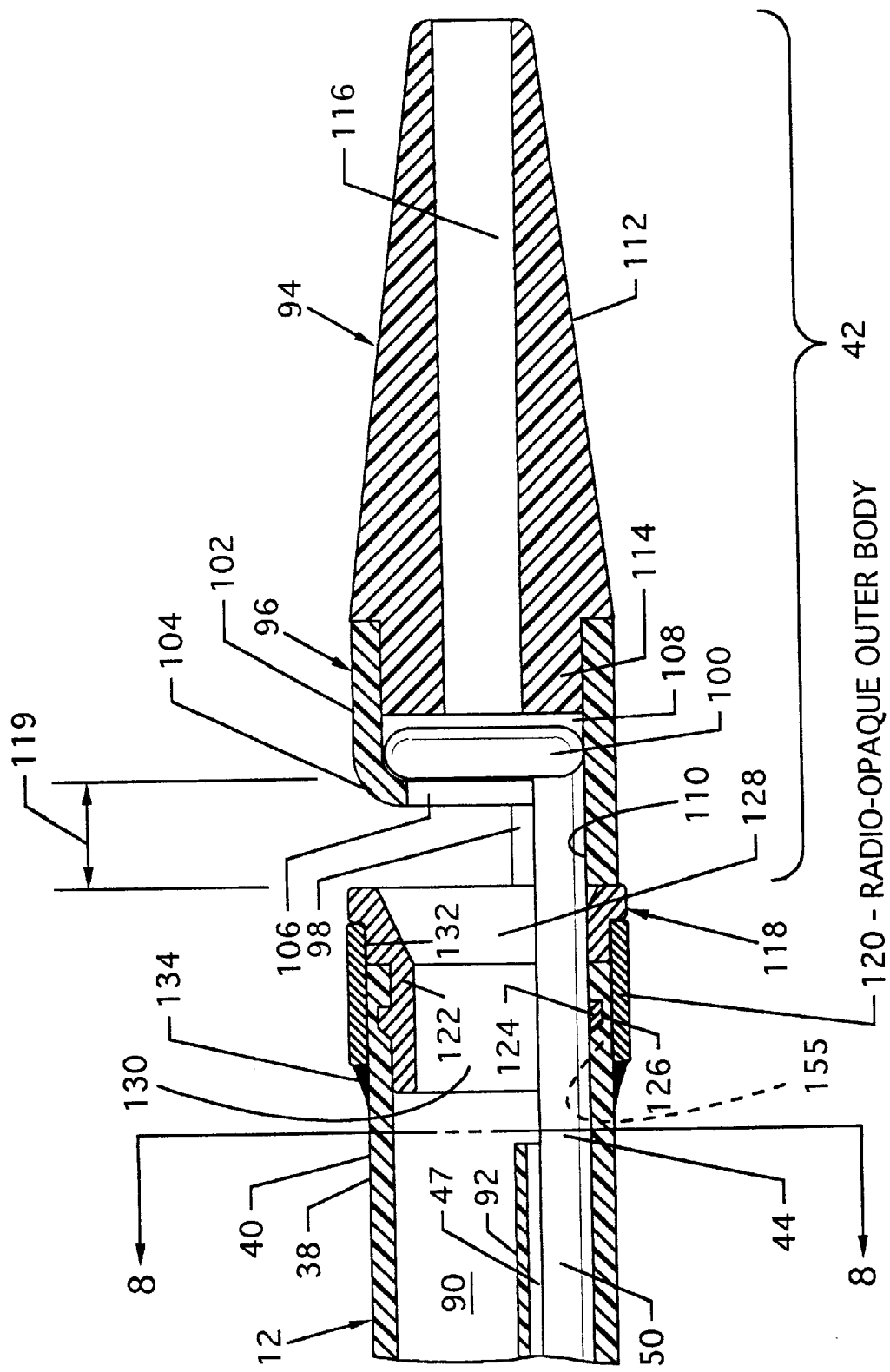
FIG. 6 is a cross section view along line 6—6 of FIG. 1 illustrating the relationship of an outer body at the dual lumen tube distal end to the flexible tip assembly.

Luer fitting 32 is utilized to secure the strain relief 36 and the dual lumen tube 38 to the distal manifold end 34. The strain relief 36 is comprised of a tube 78 having a central bore 80 which accommodates the dual lumen tube 38, an external annular flange 82, and a tapered proximal tube mouth end 84. It is to be noted that the outer diameter of the tube 78 is constant from the annular flange 82 to the distal tube end 85, and that the outer diameter of the tube 78 steadily decreases from the annular flange 82 to the tapered proximal tube mouth end 84 to provide a tapered tube surface 86 which conforms, for purpose of a proper fit, to the tapered surface 87 of the tapered centrally located main passage 52. The tapered proximal tube mouth end 84 of the tube 78 allows for easily accomplished alignment of guidewires or other assemblies with a large lumen 90 located in and extending along the interior of dual lumen tube 38. The Luer fitting 32 threadingly engages a Luer connection 88 and bears against the annular flange 82 of the strain relief 36 to force the tapered tube surface 86 of the strain relief 36 against the tapered surface 87 of the tapered centrally located main passage 52 to effect a suitable seal. A small lumen 47 (FIGS. 6 and 8) aligns in and extends along the interior of the dual lumen tube 38 parallel to the large lumen 90 and extends distally to the distal end 40 of the tubular dual lumen tube 38. The small lumen 47 accommodates the hypo-tube 44 which connects at one end to the filter housing/high pressure connection assembly 46 and at the other to the flexible tip assembly 42, as shown in FIG. 6.

Figure 4:
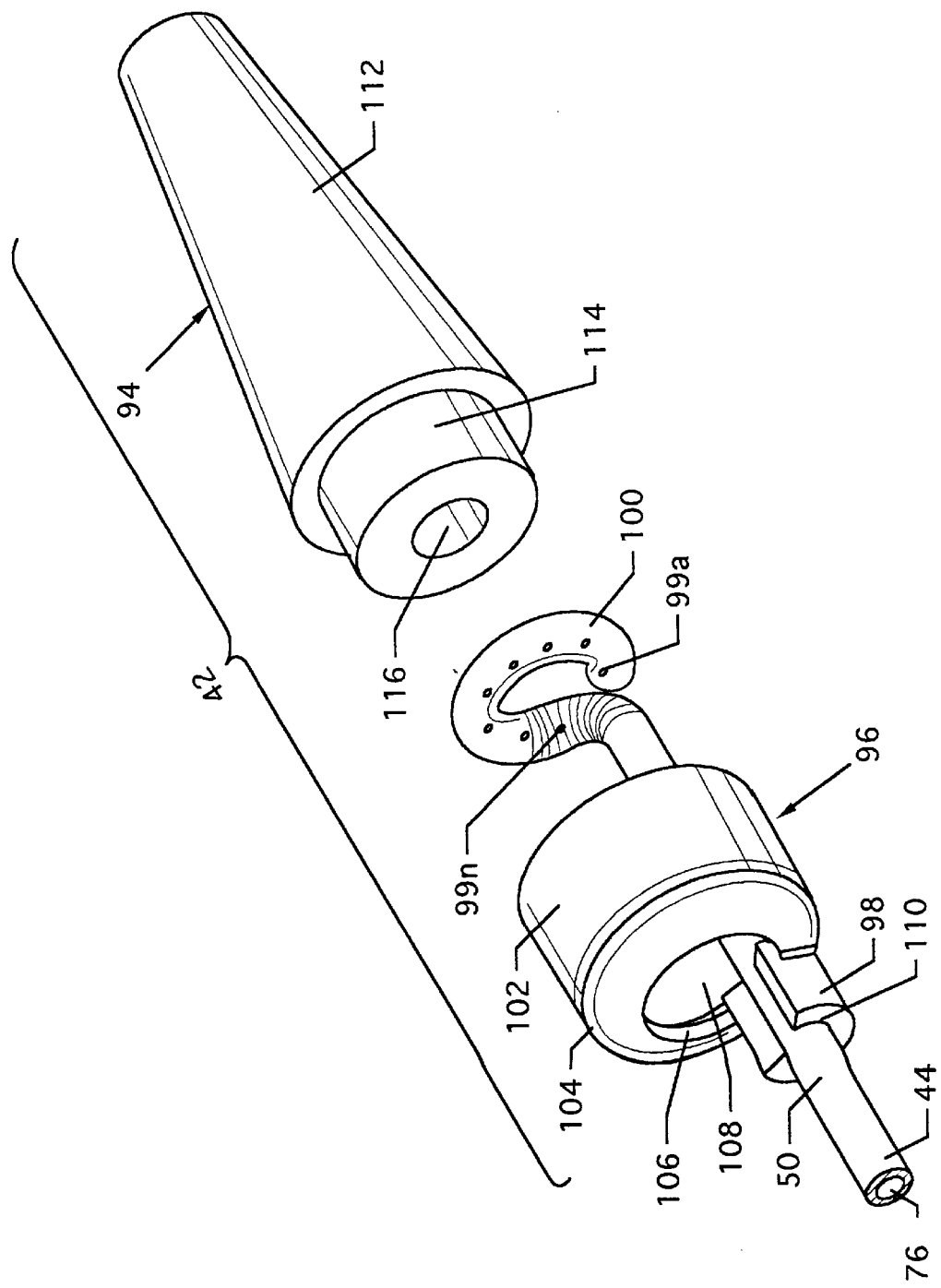
FIG. 4 is an isometric exploded view of the flexible tip assembly.
Figure 7:
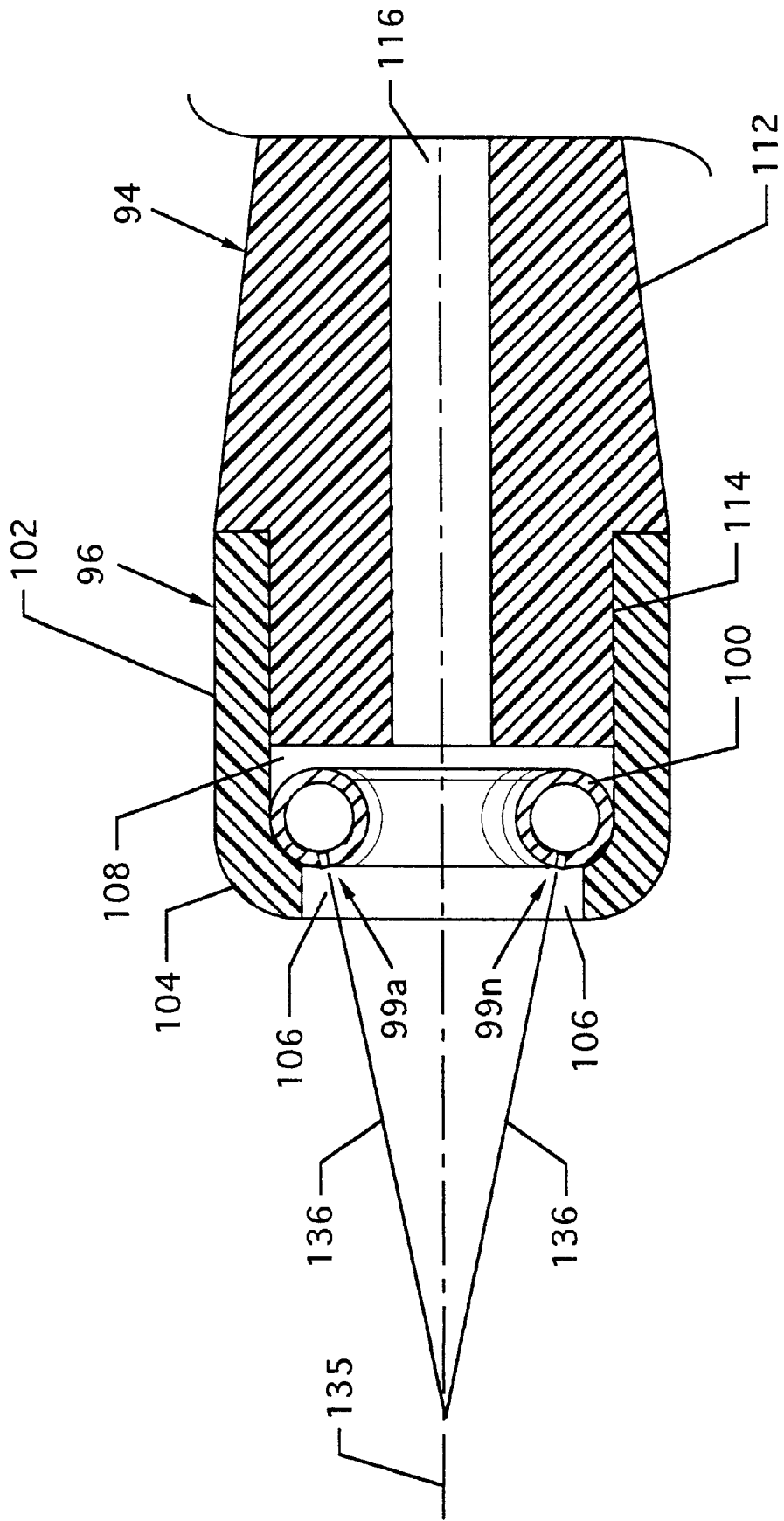
FIG. 7 is a partial cross section view of the junction of the hard plastic shell and the tapered and flexible tip.

FIG. 4 illustrates an isometric exploded view of the flexible tip assembly 42, where all numerals correspond to those elements previously or otherwise described. The flexible tip assembly 42 includes a tapered and flexible tip 94 of soft plastic polymer made of polyether block amides, or other such suitable material, and also includes a one-piece hard plastic polycarbonate shell 96 having a support extension 98 made of polycarbonate extending therefrom. A toroidal loop 100 is located at the hypo-tube distal end 50 and is housed in and fixed within the hard plastic shell 96. The toroidal loop 100 includes a plurality of jets 99a–99n on the rearward or proximally facing portion thereof each directed and/or aimed proximally at a slight inwardly projecting angle, as depicted in FIG. 7. The jets 99a–99n are located on the proximal region of the toroidal loop 100 and distributed as required along the locus of a circle having a common center with the toroidal loop 100.

The hard plastic shell 96 and support extension 98 are a one-piece structure including a cylindrical portion 102 aligned parallel to the longitudinal axis of the hypo-tube 44 and having an annular curved portion 104 extending rearwardly and inwardly from the cylindrical portion 102 to terminate substantially in a circular orifice 106. A cylindrical-like cavity 108 interior to the hard plastic shell 96 accommodates the toroidal loop 100, as later described in detail in connection with FIG. 6. The support extension 98 includes an interior curved surface 110 which accommodates and captures the hypo-tube distal end 50. Support of the hypo-tube distal end 50 is an important consideration whereby the flexible tip assembly 42 is prevented from acting as a lever arm which can result in the distortion of the 90-degree bend where the hypo-tube distal end 50 transitions to form the toroidal loop 100. Relational support of the 90-degree bend of the hypo-tube distal end 50 with respect to the toroidal loop 100 provides for proper and accurate proximal saline jet flow from the jets 99a–99n of the toroidal loop 100. The one-piece tapered and flexible tip 94 includes a tapered surface 112 and an adjoining tubular member 114. A passage 116 aligns along the axis of the tapered and flexible tip 94 and is utilized to accommodate a guidewire. The diameter of the tubular member 114 is appropriately sized to align to and fit and be secured, such as with cyanoacrylate adhesive, within the cavity 108 of the hard plastic shell 96. The respective centers of the hard plastic shell 96, the toroidal loop 100 and the passage 116 of the tapered and flexible tip 94 align about a mutual central longitudinal axis to provide a suitable guidewire path through the flexible tip assembly 42.

Figure 5:
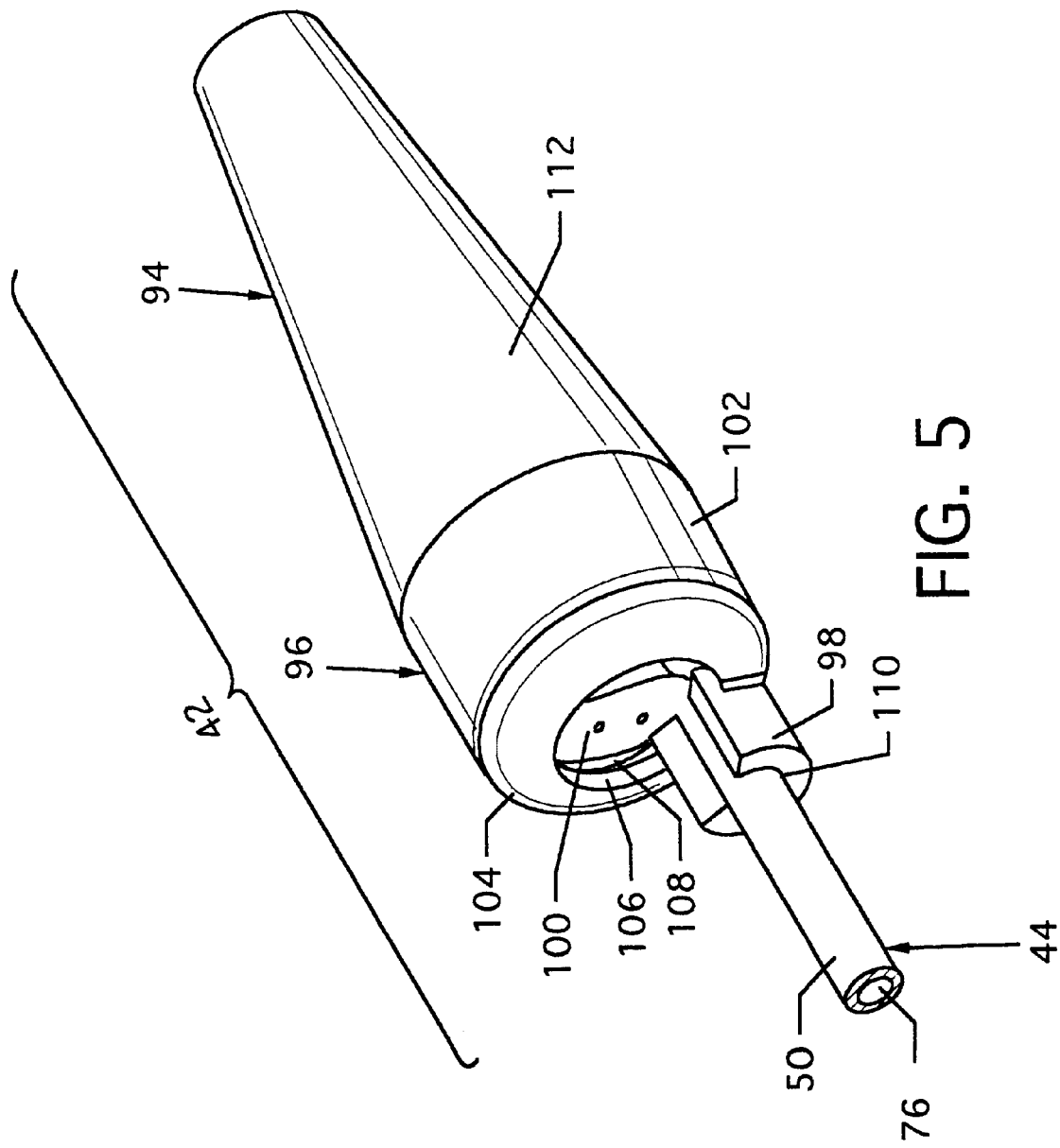
FIG. 5 is an isometric view of the assembled flexible tip assembly.

FIG. 5 illustrates an isometric view of the assembled flexible tip assembly 42, where all numerals correspond to those elements previously or otherwise described.

FIG. 6 illustrates a cross-section view along line 6—6 of FIG. 1 illustrating the relationship of an inner body 118 at the dual lumen tube distal end 40 to the flexible tip assembly 42, or stiff gap region, where all numerals correspond to those elements previously or otherwise described. The tapering of the tapered and flexible tip 94 creates a stiffness transitional zone whereby the distal tip is more flexible than those tip regions positioned proximally. Increased flexibility as well as a smaller profile or cross-section at the most distal tip region allows for better tracking about a tortuous turn. Incorporation of the hard plastic shell 96 allows a strong transitional bond and relationship to be maintained between the toroidal loop 100 and the tapered and flexible tip 94 while maintaining alignment integrity along the stiff gap region without undue stress placed across the gap 119 defined as the parallel and constant spacing between the distal annular region of the cylindrical inner body 118 and proximal annular region of the toroidal loop 100 residing in the hard plastic shell 96. Maintaining a constant and parallel spacing along and across the gap 119 is of great importance in maintaining proper flow of saline jet flow within the confines of the gap 119 and within the confines of the inner body 118. Misaligned and undesired saline flow outside of the gap 119 could impinge and undesirably cause trauma to or possibly harm or be injurious to or could puncture vessel walls. The cylindrical inner body 118 aligns to and snappingly engages the dual lumen tube distal end 40 and is further secured thereto by aid of a radio-opaque outer body 120. The inner body 118 includes a substantially annular tube 122 having an annular ring 124 thereabout which engages an annular groove 126 located on the interior of the distal end 40 of the dual lumen tube 38, an interior ramped annular inlet 128 aligned to and adjacent to a lumen 130, and an outer annular surface 132 which accommodates the radio-opaque outer body 120. Optionally, epoxy adhesive 134 is applied to smoothen transition from the outer body 120 to the dual lumen tube 38 and to aid in fastening the radio-opaque outer body 120 to the dual lumen tube distal end 40. The hypo-tube 44 aligns in and is secured, by the filter housing/high pressure connection assembly 46, in the small lumen 47 of the dual lumen tube 38, and extends, at its distal end 50, through and is offset from the center of and is tangentially adjacent to one side of the lumen 130; extends through and is offset from the center of and is adjacent to one side of the ramped annular inlet 128; extends through, is glued to, such as by cyanoacrylate adhesive, and is captured by the support extension 98; and then terminates in the toroidal loop 100 previously described. The toroidal loop 100 resides within the cavity 108 and is located and fastened by cyanoacrylate adhesive against the inner surface of the annular curved portion 104 of the hard plastic shell 96. In the alternative, the cavity 108 could include additional capture geometry to allow snap-engagement of the toroidal loop 100, with or without adhesive, in the position shown. Care is exercised in the construction process, as later described, to preclude the deposition of adhesive material on the proximally facing jets 99a–99n located proximally on the toroidal loop 100. The proximally facing jets 99a–99n align to direct saline jet flow proximally at a slight and inwardly projecting angle, as shown in FIG. 7. The saline jet flow breaks up thrombotic material which is subsequently entrained and directed by the saline jet flow through the ramped annular inlet 128 and lumen 130 of the inner body 118 and thence into the large lumen 90, which functions as an evacuation lumen, of the dual lumen tube 38 for particulate and fluid evacuation.

FIG. 7 illustrates a partial cross-section view of the junction of the hard plastic shell 96 and the tapered and flexible tip 94, where all numerals correspond to those elements previously or otherwise described. Jets 99a–99n are fashioned in the proximal side of the toroidal loop 100 and are aligned at a slight and suitable angle to the longitudinal axis 135. Saline jet flow 136 is directed at a slight inwardly projecting angle in a proximal direction from the jets 99a–99n through the orifice 106 formed between the annular curved portion 104 to break up and carry away thrombotic material, as previously described.

Figure 8:
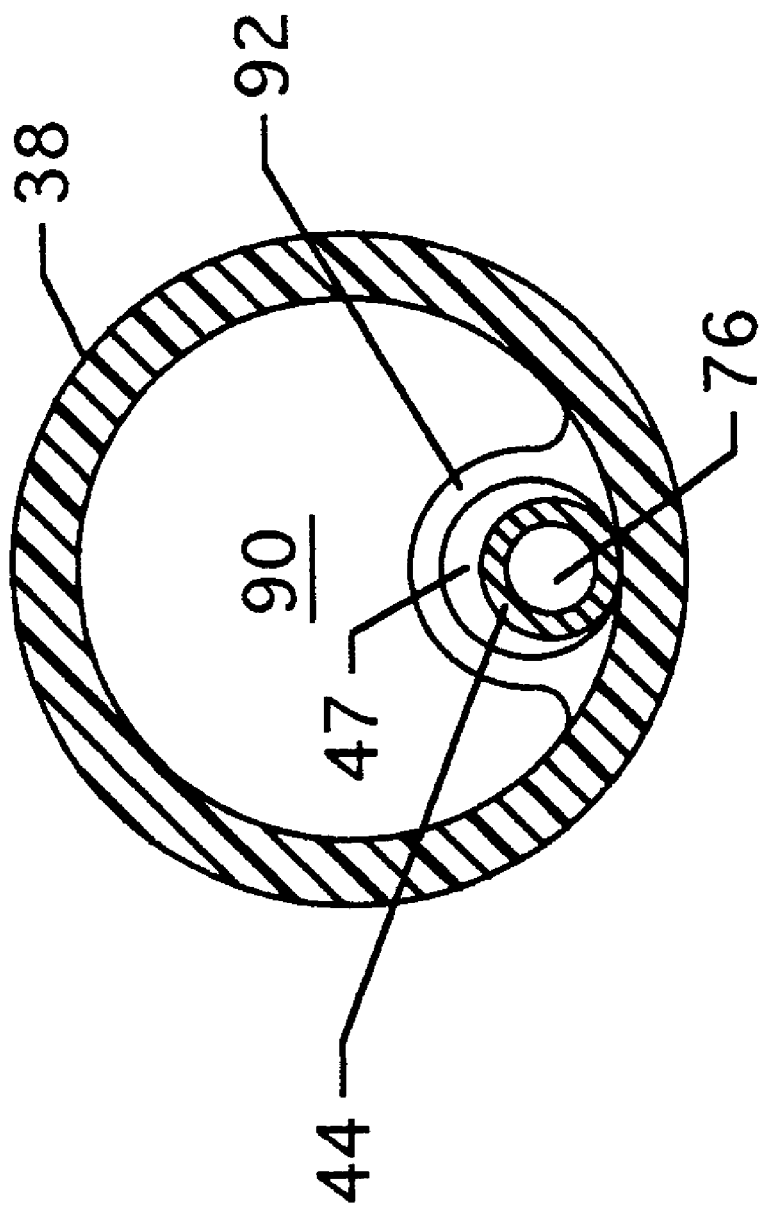
FIG. 8 is a cross section view of the dual lumen tube at the distal end along line 8—8 of FIG. 6.

FIG. 8 illustrates a cross-section view of the dual lumen tube 38 at the distal end 40 along line 8—8 of FIG. 6, where all numerals correspond to those elements previously or otherwise described. The dual lumen tube 38 is molded, extruded or otherwise formed to include an arcuate web 92 extending across the inner circumference of the dual lumen tube 38 to form the small lumen 47. The remaining area between the arcuate web 92 and the inner circumference of the dual lumen tube 38 forms the large lumen 90 which can accommodate a guidewire or which can be utilized for evacuation of saline and/or thrombotic or other particulate. Also shown is the hypo-tube 44 within the small lumen 47.

Mode of Operation

Figure 9:
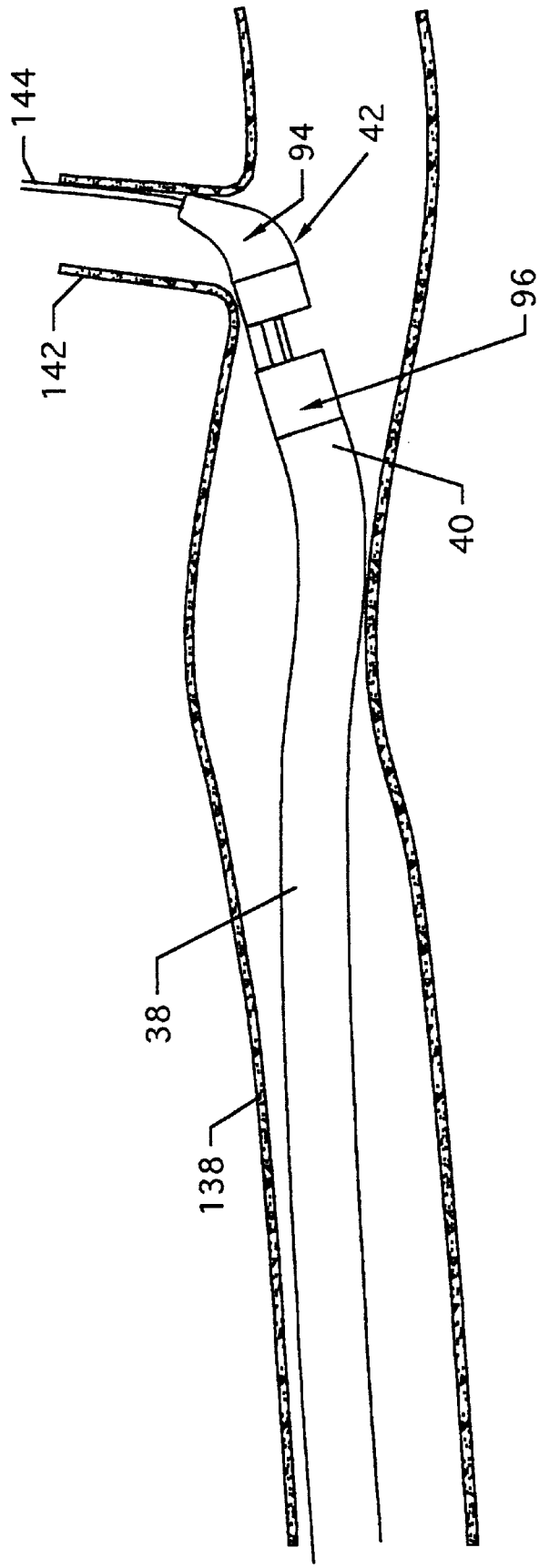
FIG. 9 is a view in cross section depicting the flexible tip assembly entering a branch artery or vessel, a tortuous path; and, FIG. 10 is a view in cross section and partial cutaway depicting the operation of the distal end of the flexible tip rheolytic thrombectomy catheter at the site of a thrombotic deposit and lesion.
Figure 10:
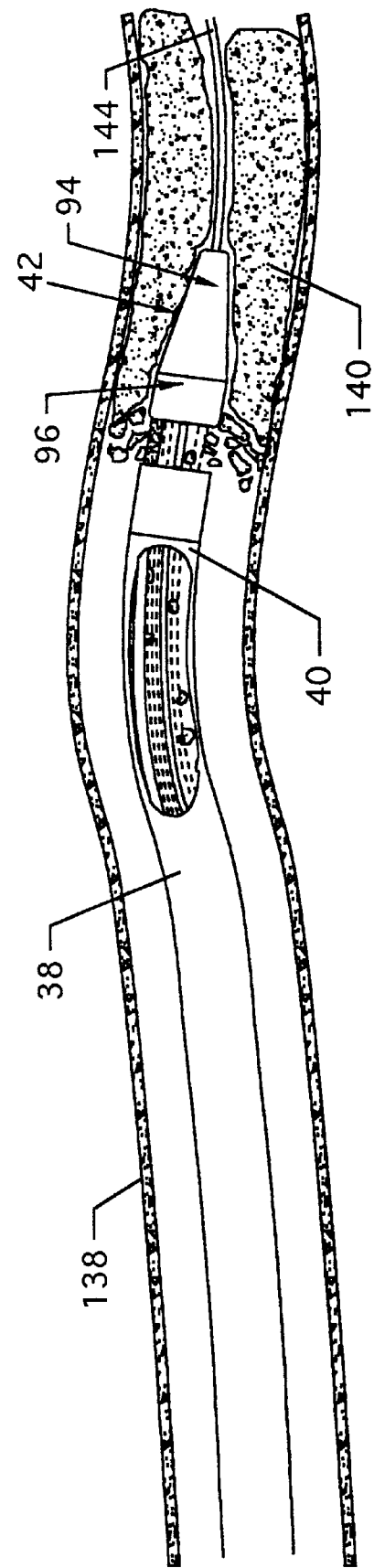

FIGS. 9 and 10 best illustrate, in cross section and/or cutaway view, the mode of operation of the flexible tip rheolytic thrombectomy catheter 10 with particular attention to the dual lumen tube distal end 40 and flexible tip assembly 42 positioned in a blood vessel 138, artery or the like, enroute to (FIG. 9), or at the site of (FIG. 10) a thrombotic deposit and lesion 140 (FIG. 10). FIG. 9 shows the flexible tip assembly 42 entering a branch artery or vessel 142, a tortuous path, and FIG. 10 shows the operation of the distal end 40 of the dual lumen tube 38 of the flexible tip rheolytic thrombectomy catheter 10 at the site of a thrombotic deposit and lesion 140. Once the distal end 40 of the dual lumen tube 38 reaches a thrombotic deposit and lesion, whether in the main artery or vessel or branch artery or vessel, the oblation function is started and is similar in both regions.

A guidewire 144 is first advanced percutaneously through the tortuous vasculature, such as through the blood vessel 138 and then into the branch artery or vessel 142, to the site of the thrombotic deposit and lesion such as or similar to the thrombotic deposit and lesion 140. For a distal coronary vessel, typically the guidewire has a diameter of 0.014 to 0.018 inch. Once a guidewire 144 has been advanced along the vessel 138 and has reached the thrombotic deposit and lesion 140, the flexible tip catheter 10 can be advanced over the guidewire 144 by introducing the proximal guidewire end through passage 116 (FIG. 6) and through exhaust lumen 90, passage 52, and passage 60, and other associated components to subsequently allow the flexible tip rheolytic catheter 10 to negotiate tortuous turns such as that at branch artery or vessel 142 to reach the thrombotic deposit and lesion 140.

The main passage 52 of the manifold 16 and the exhaust lumen 90 of the dual lumen tube 38 serve as an evacuation tube. The rheolytic thrombectomy catheter 10 can then be activated by providing high pressure liquid, preferably saline, to the proximal end of the dual lumen tube 38 via the manifold 16.

High pressure saline, or other liquid, from the manifold 16 is provided and flows through the lumen 76 of the hypo-tube 44 to exit jets 99a–99n of the toroidal loop 100. The high pressure saline jet flow 136 exits the jets 99a–99n as retrograde jets of high velocity saline each being directed at a slight angle through the gap 119 and toward the ramped annular inlet 128 and lumen 130 of the inner body 118 and into the large lumen 90 of the dual lumen tube 38 for subsequent evacuation. Saline jet flow 136 from the high velocity saline jets 99a–99n dislodges tissue from the thrombotic deposit and lesion 140 and entrains it into the saline jet flow 136 where it is broken up into smaller fragments. Impingement of the saline jet flow 136 onto the dual lumen tube distal end 40 creates a stagnation pressure within the large lumen 90 that drives the debris particles of tissue from the thrombotic deposit and lesion 140 toward the proximal end of the dual lumen tube 38.

A positive displacement piston pump (not illustrated) can be used to provide liquid, preferably saline, under pressure to the hypo-tube proximal end 48 via the filter housing/high pressure connection assembly 46 at the manifold branch 24. A pressure ranging from 500–15,000 psi will provide the energy to create a useful high velocity jet as the saline exits the jets 99a–99n located at the proximal side of the toroidal loop 100. The flow rate of saline can be controlled by adjusting the pumping rate of the positive displacement piston pump. The proximal end of the dual lumen tube 38 interfaces with a metering device, such as a roller pump, through the Luer connection 26 at the manifold branch 30 prior to discharge of the evacuated thrombotic debris into a collection bag for disposal. The rate of evacuation can be controlled by adjusting the rate of a roller pump (not illustrated) connected to the manifold branch 30. The rate of saline inflow can be balanced with the rate of removal of thrombotic debris by simultaneous adjustment of the piston pump and the roller pump. The rate of saline inflow can be less than, equal to, or greater than the rate of removal of thrombotic debris. The rate of thrombus removal can be set to slightly exceed the rate of saline inflow to reduce the likelihood for distal embolization of thrombotic tissue.

Method of Construction

The flexible tip rheolytic thrombectomy catheter 10 contains a high pressure hypo-tube 44 which is drawn down proximally to distally in successively smaller diameters which results in increased flexibility over a limited length. The hypo-tube 44 is then closed on the distal end with a plasma weld technique. This distal end 40 is then fashioned into a 90-degree bend of an appropriate length and then looped into a toroidal loop 100 of chosen dimensions. When these activities have been sufficiently concluded, hypo-tube 44 is threaded proximal end first through orifice 106 of the hard plastic shell 96. The shell 96 is snappingly engaged with the toroidal loop 100 and the hypo-tube distal end 50 engages the support extension 98. The shelled toroidal assembly is then appropriately inserted into a specialized tool such that all of the jets 99a–99n are masked such that they will not become occluded when cyanoacrylate adhesive is deposited onto the interface of the toroidal loop 100 and cavity 108 of the hard plastic shell 96 which is done to produce an appropriate bond intensity between the toroidal loop 100 and the hard plastic shell 96 that is required by the design. This assembly is further constructed by adding a concentrically affixed inner body 118 by way of alignment slot 155, in relation to the toroidal loop 100 and hard plastic shell 96, to the hypo-tube 44 such as to produce an optimally scaled gap 119. A radio-opaque outer body 120 is then guided into position over the outer diameter of the distal end 40 of the dual lumen tube 38 such that the dual lumen tube 38 is compressively held. Optionally, this joint is further improved by the use of epoxy adhesive 134 or cyanoacrylate or another suitable material. The transition between the outer body 120 and dual lumen tube 38 is minimized by the use of epoxy adhesive 134 or another suitable adhesive or with a sufficiently tapered outer body 120. The tapered and flexible tip 94 which is also made of a polyether block amide polymer or another suitable flexible and possibly soft material can be attached at any point in the process but is optimally attached at a point in the process to minimize the agglomeration of foreign material to its tapered surface 112. Cyanoacrylate or another appropriate adhesive is applied controllably and effectively to the flexible tip tubular member 114. The tapered and flexible tip 94 is then mechanically inserted into an appropriately mated cavity 108 of the hard plastic shell 96 which is done to produce an appropriate bond intensity between the hard plastic shell 96 and the tapered and flexible tip 94 that is required by the design. The previously described assembly is then either proximally inserted into the manifold 16 into passage 52, through passage 54 or distally through passage 54 and then passage 52. After this operation, the suitably preassembled filter housing/high pressure connection 46 is affixed to the hypo-tube proximal end 48 by way of a compressive anchoring plug 74. The strain relief 36 is placed over the proximal end of the dual lumen tube 38. The tapered surface 86 of the strain relief 36 which is composed of a proper flexible material is then compressively captured and seated so as to produce an appropriate seal against tapered surface 87 and dual lumen tube 38 of the manifold 16 by way of Luer fitting 32 which mechanically advances the strain relief 36 by way of physical interference of the annular flange 82 and the torquedly advanced Luer fitting 32. The filter housing/high pressure connection 46 is similarly seated and sealed against tapered surface 155 of passage 54 by way of Luer fitting 61. These seals are designed such that pressures of 0 to 300 psi can be easily contained without the aid of further intervention by way of adhesive or another similar substance. The O-ring 58 and hemostasis nut 18 can be positioned into manifold 16 at any point in the assembly operation. The flexible tip rheolytic thrombectomy catheter 12 which has been assembled to the previously described degree then is allowed to continue on into normal catheter testing, packaging, etc. procedures.

Flexible Tip Rheolytic Thrombectomy Catheter and Method of Constructing Same

| | | | |
|---|---|---|---|
| 10 | flexible tip rheolytic thrombectomy catheter | 44a-n | hypo-tube portion |
| 12 | outer assembly | 45 | small lumen |
| 14 | inner assembly | 46 | filter housing/high pressure connection assembly |
| 16 | manifold | | |
| 18 | hemostasis nut | 47 | small lumen |
| | | 48 | hypo-tube proximal end |
| 20 | manifold proximal end | 50 | hypo-tube distal end |
| 22 | Luer connection | 52 | passage (main) |
| 23 | proximal end | 54 | passage (branch 24) |
| 24 | manifold branch | 55 | passage (branch 30) |
| 26 | Luer connection | | |
| 28 | proximal end | 56 | multi-radius cavity |
| 30 | manifold branch | 58 | O-ring |
| 32 | Luer fitting | 60 | passage |
| 34 | distal end | 61 | Luer fitting |
| 36 | strain relief | 62 | body |
| 38 | dual lumen tube | 64 | threaded surface |
| 40 | distal end | 66 | tubular cavity |
| 42 | flexible tip assembly | 68 | fine filter |
| 44 | high pressure second or hypo-tube | 70 | coarse filter |
| | | 72 | passage |
| | | 74 | anchoring plug |
| 76 | lumen (hypo-tube) | 114 | tubular member |
| 78 | tube | 116 | passage |
| 80 | bore | 118 | inner body |
| 82 | annular flange | 119 | gap |
| 84 | tapered proximal tube mouth end | 120 | radio-opaque outer body |
| | | 122 | annular tube |
| 85 | distal tube end | 124 | annular ring |
| 86 | tapered tube surface | 126 | annular groove |
| 87 | tapered surface | 128 | ramped annular inlet |
| 88 | Luer connection | 130 | lumen |
| 90 | exhaust lumen (large) | 132 | annular surface |
| 92 | arcuate web | 134 | epoxy adhesive |
| 94 | tapered and flexible tip | 135 | longitudinal axis |
| | | 136 | saline jet flow |
| 96 | hard plastic shell | 138 | blood vessel |
| 98 | support extension | 140 | thrombotic deposit and lesion |
| 99a-n | jets | | |
| 100 | toroidal loop | 142 | branch artery or vessel |
| 102 | cylindrical portion | 144 | guidewire |
| 104 | annular curved portion | 155 | tapered surface |
| 106 | orifice | | |
| 108 | cavity | | |
| 110 | curved surface | | |
| 112 | tapered surface | | |

Various modifications can be made to the present invention without departing from the apparent scope hereof.

It is claimed:

1. A rheolytic thrombectomy catheter for the removal of thrombus from a body vessel having a high pressure hypo-tube, the end of which is formed into a toroidal loop having a plurality of inwardly directed jets for directing a flow of pressurized fluid to impinge on, and carry, a dislodged thrombus into an exhaust/evacuation tube, the improvement comprising;

a. rigid tubular shell positioned adjacent said toroidal loop;

b. an aperture in said rigid tubular shell aligned to permit fluid carrying dislodged thrombus to enter a gap proximal to said rigid tubular shell wherein said dislodged thrombus is propelled into the distal end of an axially centered exhaust/evacuation tube; and, c. a flexible tip member at the distal end of said rigid tubular shell, said flexible tip member having a tip of reduced diameter at the distal end thereof and a reduced diameter shoulder portion positioned within said rigid tubular shell and affixed thereto, whereby the distal end of said flexible tip member follows turns in said vessel and said rigid tubular shell prevents distortion of said toroidal loop as said catheter is inserted into said vessel.

2. The catheter of claim 1, wherein said rigid tubular shell is affixed to said toroidal loop.

3. The catheter of claim 2, wherein said rigid tubular shell is affixed to said toroidal loop with an adhesive.

4. The catheter of claim 3, wherein said adhesive is an cyanoacrylate.

5. The catheter of claim 2, wherein said rigid tubular shell includes a stem portion extending proximally and providing support for said high pressure hypo-tube at a point proximal of said toroidal loop.

6. The catheter of claim 5, wherein said stem portion is axially displaced from the center of said rigid tubular shell and having a diameter less than half the diameter of a remainder of said rigid shell and a centrally located hole to accommodate said high pressure hypo-tube.

7. The catheter of claim 6, wherein said stem portion supports said high pressure hypo-tube in a region displaced from said toroidal loop thereby preventing distortion of said toroidal loop from a transverse axial alignment with respect to a longitudinal portion of said high pressure hypo-tube.

8. The catheter of claim 2, wherein said rigid tubular shell is a hard plastic material.

9. The catheter of claim 8, wherein said hard plastic material is polycarbonate.

10. The catheter of claim 2, wherein said flexible tip member is a soft polymer plastic material.

11. The catheter of claim 10, wherein said soft polymer plastic material is polyurethane.

12. The catheter of claim 1, wherein said aperture in said rigid tubular shell comprises an annular slot extending partially around said rigid tubular shell.

13. The catheter of claim 1, wherein said flexible tip member includes an axially positioned hole extending therethrough.

14. The catheter of claim 13, wherein said axially positioned hole has a diameter sufficient to accommodate a guidewire during insertion of said catheter into a body vessel.

15. The catheter of claim 14, further including a guidewire passing through said axially positioned hole in said flexible tip member.

16. The catheter of claim 15, wherein said guidewire passes though said exhaust/evacuation tube.

17. The catheter of claim 1, further including an exhaust/evacuation tube surrounding said high pressure hypo-tube and connected to said catheter.

18. The catheter of claim 17, further including a cylindrical outer shell affixed to the hypo-tube on a location proximal to said rigid tubular shell.

19. The catheter of claim 18, wherein said exhaust/evacuation tube is affixed to said outer shell.

* * * * *

UNITED STATES PATENT AND TRADEMARK OFFICE
CERTIFICATE OF CORRECTION

| | |
|---|---|
| PATENT NO. | : 5,989,271 |
| APPLICATION NO. | : 09/188631 |
| DATED | : November 23, 1999 |
| INVENTOR(S) | : Bonnette et al. |

It is certified that error appears in the above-identified patent and that said Letters Patent is hereby corrected as shown below:

ON THE TITLE PAGE

Item (75), Under "Inventors", in Column 1, Line 1, delete "Steven E. Wiesel" and insert -- Stephen E. Weisel --, therefor.

Signed and Sealed this

Second Day of June, 2009

JOHN DOLL
*Acting Director of the United States Patent and Trademark Office*